(12) United States Patent
Netzhammer

(10) Patent No.: US 10,646,901 B2
(45) Date of Patent: May 12, 2020

(54) CLEANING DEVICE FOR SMALL PARTS

(71) Applicant: Eric Netzhammer, Arlesheim (CH)

(72) Inventor: Eric Netzhammer, Arlesheim (CH)

( * ) Notice: Subject to any disclaimer, the term of this patent is extended or adjusted under 35 U.S.C. 154(b) by 0 days.

(21) Appl. No.: 15/537,077

(22) PCT Filed: Dec. 18, 2015

(86) PCT No.: PCT/EP2015/080440
§ 371 (c)(1),
(2) Date: Jun. 16, 2017

(87) PCT Pub. No.: WO2016/097265
PCT Pub. Date: Jun. 23, 2016

(65) Prior Publication Data
US 2017/0348737 A1    Dec. 7, 2017

(30) Foreign Application Priority Data
Dec. 18, 2014    (CH) ........................................ 1973/14

(51) Int. Cl.
*A61L 2/26*    (2006.01)
*B08B 3/04*    (2006.01)
*B08B 13/00*   (2006.01)
*A61L 2/18*    (2006.01)

(52) U.S. Cl.
CPC ............. *B08B 3/044* (2013.01); *A61L 2/18* (2013.01); *A61L 2/26* (2013.01); *B08B 13/00* (2013.01); *A61L 2202/17* (2013.01); *A61L 2202/24* (2013.01)

(58) Field of Classification Search
CPC .... A61L 2/26; A61L 2202/17; A61L 2202/24; B08B 3/044; B08B 13/00
USPC ...................... 134/115 R, 120, 133, 137, 200
See application file for complete search history.

(56) References Cited

U.S. PATENT DOCUMENTS

| | | |
|---|---|---|
| 6,659,115 B1 | 12/2003 | Wieczorek |
| 2007/0069087 A1 | 3/2007 | Mumm |
| 2011/0240069 A1 | 10/2011 | Netzhammer |

FOREIGN PATENT DOCUMENTS

| | | |
|---|---|---|
| DE | 94 21 818 U1 | 11/1996 |
| DE | 44 09 659 A1 | 10/2000 |
| EP | 1 789 889 A1 | 4/2007 |
| EP | 2 502 636 A1 | 9/2012 |
| WO | WO 00/61199 A1 | 10/2000 |
| WO | WO 00/74735 A1 | 12/2000 |
| WO | WO 2010/040383 A1 | 4/2010 |

OTHER PUBLICATIONS

Peper, "DE4409659A1 English Machine Translation.pdf", Sep. 28, 1995—Machine translation from Espacenet.com.*
International Search Report for PCT/EP2015/080440 dated Mar. 9, 2016.

* cited by examiner

*Primary Examiner* — Levon J Shahinian
(74) *Attorney, Agent, or Firm* — Birch, Stewart, Kolasch & Birch, LLP

(57) ABSTRACT

The cleaning device for small parts has a treatment container which is permanently attached to a carriage and is rotatably mounted on the carriage. It can be docked with a treatment station while remaining on the carriage.

1 Claim, 2 Drawing Sheets

CLEANING DEVICE FOR SMALL PARTS

The invention relates to a device for the gentle cleaning, sterilization and drying of large numbers of small parts. These parts can, for example, be parts of syringes or vials, i.e. predominantly parts which are used in the medical field.

To carry out these processes various devices and methods are known, which, however, have disadvantages either with respect to the methods or with respect to the design of the device.

A known device consists of a rotating, permanently installed treatment container with a screen plate and/or a fine-mesh screen serving as support for the small parts. The media that are needed to carry out the treatment flow through said screen plate and generate a so-called fluidized bed which causes the treatment. After treatment has taken place, the parts are transferred to so-called transport containers, while maintaining sterility, and stored therein until said parts are delivered to a subsequent device.

Another known device consists of a carriage and a container placed therein. Said container must be docked with a treatment machine and the carriage is removed for the treatment operation such that the container can be rotated when in docked state. After the treatment operation, the container is undocked again and brought back into the carriage.

This process is complicated, on the one hand, from a constructive and mechanical point of view and, on the other hand, such docking and undocking processes carry risks for the operator and are impractical. Another disadvantage of this device is that the rotatability of the container—which is strictly necessary for the treatment—is only given when on the treatment machine.

Moreover, the inspection of the container on such devices is very complicated. Since the container in the carriage cannot be rotated, the container has to be lifted using e. g. a separate lifting device and rotated such that it is possible to look into the container.

Loading this known device is difficult as well. Furthermore, complete emptying on the overflow side is not possible either due to the limited rotatability of the container. The washing liquid must then be emptied downwards and this soils the screen plate and the clean inlet side e. g. with particles.

Also, it is complicated to remedy a batch loss in the known devices. Since the container in the carriage cannot be rotated, the container must be lifted using e. g. a separate lifting device and rotated into the discharge position so that the lost batch can be emptied.

The object of the invention is to avoid the above-mentioned disadvantages of the prior art.

According to the invention, this is achieved by means of a device of the above-mentioned type characterized by the characterizing features of claim 1.

Subsequently, a preferred embodiment of the inventions is illustrated in the accompanying drawings. In which.

Figure 1:
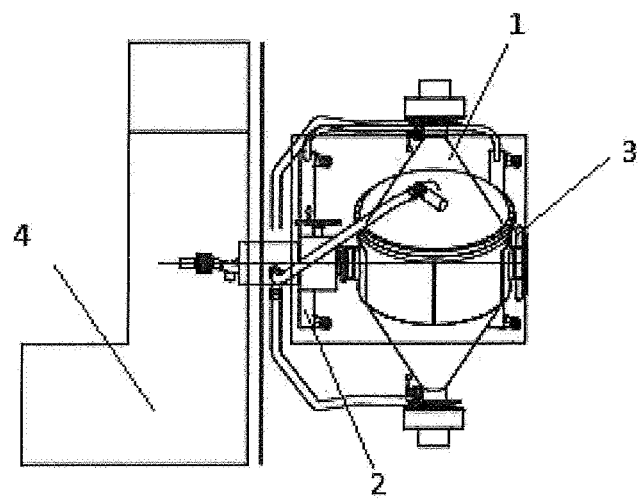
FIG. 1 shows a top view of a device according to the invention
Figure 2:
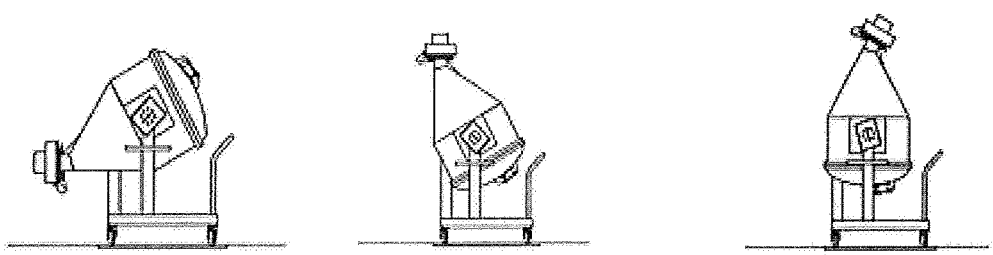
FIG. 2 shows side views of said device with different container positions.

The device shown in the drawings consists of a treatment container 1 and a transport carriage 2 to which the treatment container is permanently attached, i. e. a container and a carriage form a respective unit. The container is rotatably mounted on the carriage by bearing means 3. The bearings are configured to enable rotation of the container axis by 240°. Furthermore, one of the bearings is equipped with means known per se for docking the container with a treatment station 4.

By means of carefully rotating the container on the carriage, a gentle treatment of the small parts will be achieved. The draining of remaining water and condensate and the draining of cavities in the small parts which is required for consistent treatment quality is also achieved by carefully rotating the container. For complete draining, the container axis in the carriage can be rotated to minus 150° and the washing water can be driven out by compressed air. Thanks to this draining feature all particles that were flushed out during washing can be completely removed preventing any back-flow of the washing medium.

If the fluidized bed is switched off (fluidizing air off), the excess air pressure below the screen is still sufficient such that the water flowing in displaces the air and prevents any back-flow towards the direction of the screen.

Figure 3:
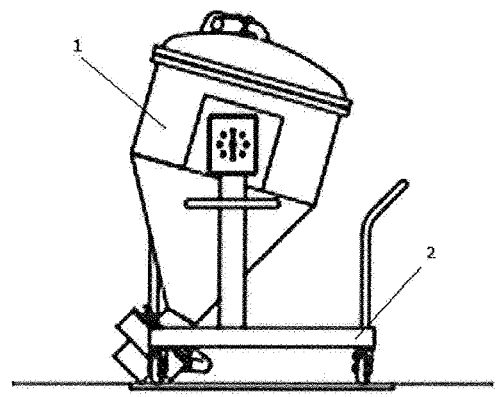
FIG. 3 shows the device with the container in the emptying position

Directly following the washing process, the machine is rotated into the emptying position shown in FIG. 3 such that the washing water can be pushed out completely to the waste water side. Due to the fact that the container can be completely drained downwards, the clean supply line and the screen plate are not traversed with dirty water.

Figure 4:
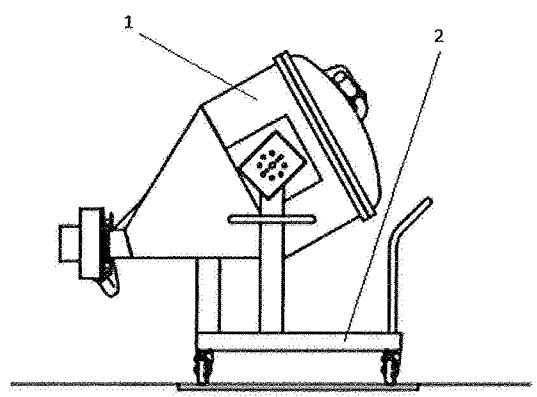
FIG. 4 shows the device with the container in the inspection position

The carriage also serves as inspection device. In the carriage, the container can be rotated downwards into the position shown in FIG. 4 so as to enable easy access to the container for inspecting the interior of the container. If remaining parts are found in the container, they can be discharged by further rotating the container downwards.

In case of a batch loss, the container on the carriage can be rotated into the discharge position and the small parts can be discharged downwards without using an additional device.

The invention claimed is:

1. A device for the gentle cleaning, sterilization and drying of large numbers of small parts, said device comprising
 a container in which the treatment of the small parts is carried out, and
 a wheeled and freely movable transport carriage to which said container is permanently and rotatably mounted,
 said carriage comprising bearings configured to enable rotation of the container axis by from minus 150° up to 240°, provided that one of the bearings is additionally configured for docking the container together with the carriage to a treatment station.

* * * * *